United States Patent [19]

Almasi

[11] Patent Number: 5,274,549
[45] Date of Patent: Dec. 28, 1993

[54] METHOD OF DERIVING A CARDIAC EJECTION FRACTION FROM NUCLEAR IMAGE DATA

[75] Inventor: John J. Almasi, Waukesha, Wis.

[73] Assignee: General Electric Company, Milwaukee, Wis.

[21] Appl. No.: 525,528

[22] Filed: May 18, 1990

[51] Int. Cl.$^5$ .......................... G06F 15/00; A61B 5/05
[52] U.S. Cl. .............................. 364/413.07; 128/659; 128/713; 382/6; 364/413.13
[58] Field of Search ............... 364/413.07; 128/653.1, 128/659, 661.1, 661.08, 661.09, 713, 672, 694, 691; 382/6

[56] References Cited

U.S. PATENT DOCUMENTS

| | | | |
|---|---|---|---|
| 4,245,646 | 1/1981 | Ionnou et al. | 128/653 |
| 4,245,647 | 1/1981 | Randall | 128/659 |
| 4,294,259 | 10/1981 | Picunko et al. | 128/653 |
| 4,295,473 | 10/1981 | Diamond et al. | 178/695 |
| 4,326,539 | 4/1982 | Obermajer | 128/713 |
| 4,331,869 | 5/1982 | Rollo | 250/2524 |
| 4,404,973 | 9/1983 | Lancaster et al. | 128/654 |
| 4,528,453 | 7/1985 | Heller | 250/505 |
| 4,680,628 | 7/1987 | Wojcik et al. | 358/111 |
| 4,716,904 | 1/1988 | Meno | 128/659 |
| 4,729,379 | 3/1988 | Ohe | 128/654 |
| 4,730,212 | 3/1988 | Wojcik et al. | 358/83 |
| 4,879,652 | 11/1989 | Nowak | 364/413.18 |
| 5,065,435 | 11/1991 | Oe | 382/6 |
| 5,072,384 | 12/1991 | Doi et al. | 364/413.13 |

OTHER PUBLICATIONS

"R-Wave Synchronized Blood-Pool Imaging" by S. G. Sorenson et al., Radiology, May 1979.
"Multiple Gated Cardiac Blood Pool Imaging for Left Ventricular Ejection Fraction:Validation of the Technique and Assesment of Variability" by F. J. Wackers et al., The American Journal of Cardiology, Jun. 1979.
Advertisement from a 1982 issue of Radiology.
"Clinical Validation of Fully Automated Computation of Ejection Fraction from Gated Equilibrium Blood-Pool Scintigrams", by J. H. C. Reiber et al., The Journal of Nuclear Medicine, vol. 24, No. 12, 1983.

Primary Examiner—Roy N. Envall, Jr.
Assistant Examiner—Xuong Chung
Attorney, Agent, or Firm—Quarles & Brady

[57] ABSTRACT

A series of nuclear images of a heart is acquired and stored in a memory device. One of the images is assumed to have occurred at the diastole and the perimeter of the left ventricle in this image is found. This perimeter is applied to the image series to produce a sum of the radiation counts within the perimeter for each image. If the maximum count sum is not produced by the image from which the perimeter was found, a new perimeter and a new maximum count sum are produced specifically for that maximum count sum image. A group of five consecutive images, which include the image from which the minimum count sum was produced, is defined. For each image in this group the left ventricle perimeter and the sum of enclosed radiation counts are individually produced. The smallest of these latter sums is used with the maximum count sum to derive the cardial ejection fraction.

14 Claims, 4 Drawing Sheets

METHOD OF DERIVING A CARDIAC EJECTION FRACTION FROM NUCLEAR IMAGE DATA

BACKGROUND OF THE INVENTION

The field of the invention is imaging systems used in the practice of nuclear medicine, and more specifically to the determination of a cardiac ejection fraction from a sequence of nuclear images of a heart.

Nuclear imaging systems such as those described in U.S. Pat. Nos. 4,497,024 and 4,652,758 include a sensor, or camera, which is sensitive to emissions from radioactive substances introduced into a patient. The camera can be held stationary to produce a single anatomical view or rotated about the patient to produce a series of views from different angles. To produce each view, the camera senses the magnitude of the radiation received from the patient at a two-dimensional array of sensing points, thereby producing an equivalent number of data samples. The relative magnitude of each radiation sample can be used as a picture element to construct a two-dimensional image of the patient anatomy.

Images produced by these cameras are used in cardiology to evaluate heart function. In performing this evaluation, the radiologist injects a radio pharmaceutical into the patient's blood stream. The substance emits gamma rays as it is carried throughout the patient's body by the blood flow. During the cardiac cycle, the heart fills with blood thereby concentrating a significant amount of the radio pharmaceutical in the heart cavities. The images produced by counting the gamma radiation emanating from the chest of the patient clearly show the heart cavities which can easily be distinguished from blood vessels and other organs. A series of these images often is produced depicting the heart at different stages of the cardiac cycle.

From this series of images, the cardiac ejection fraction can be calculated as one parameter of heart performance. The cardiac ejection fraction is the average fractional decrease in blood volume of the heart as it beats. An example of a system for deriving this parameter is described in a paper by J. H. C. Reiler et al. entitled "Clinical Validation of fully Automated Computation of Ejection Fraction from Gated Equilibrium Blood-Pool Scintigrams" which appeared in Volume 24, page 1099 of The Journal of Nuclear Medicine (1983). In order to calculate the cardiac ejection fraction, the blood volumes of the heart's left ventricle is derived at the diastole and the systole of the cardiac cycle. The initial step in finding these volumes involves filtering the image data samples and using conventional edge detection and contour extraction techniques to determine the perimeter of the heart chambers. Several well known pattern recognition techniques have been used to locate the left ventricle perimeter in the image. The data samples within the perimeter of the left ventricle then are summed to provide a numerical value proportional to the left ventricle blood volume in that image, once extraneous background artifacts affecting the data samples have been taken into account.

The most accurate method for determining the cardiac ejection fraction requires deriving the left ventricle blood volume indication for every image taken during a cardiac cycle. The image for which the sample sums are the largest and the smallest depict the heart at diastole and systole, respectively. As 16 to 32 images typically are taken during a cardiac cycle, with more images providing greater accuracy, deriving the ejection fraction becomes a very time consuming, non-real time process.

As a consequence, an approximation technique is often used in place of individually calculating the left ventricle count sum for each cardiac cycle image, in order to decrease the evaluation time. For this technique, the QRS complex or the R-wave of an electrocardiogram signal produced by heart activity is employed as a reference point for initiating the acquisition of images. By properly timing the image acquisition with respect to this signal, the first image acquired usually depicts the heart near or at the diastole. The perimeter of the left ventricle of the first image is determined and the gamma radiation count samples which lie within that perimeter are summed. This sum is assumed to represent the diastolic blood volume. Instead of determining the left ventricle perimeter for each image in the series, the perimeter from the first image is used to select the count samples to sum for each remaining image. The smallest sum is considered to be the systolic blood volume and is used with the sum for the first image in computing the ejection fraction.

Although this latter process provides a reasonably accurate approximation of the ejection fraction, some discrepancy can exist between the approximated fraction and the actual value. For example, the first image in the series may not have been taken when the actual diastole occurred. In addition, since the left ventricle perimeter of the first image is used in deriving the count summation in subsequent images, other heart chambers and anatomical elements can enter the area defined by that perimeter as the heart contracts in those images. In this case, the count sum for the true systolic image may include count samples from these elements and have a greater magnitude than another image. Thus, the approximation technique may select the incorrect image as occurring at the systole.

SUMMARY OF THE INVENTION

A nuclear imaging apparatus produces a series of images of a heart during a cardiac cycle. Each image is formed by a plurality of radiation counts representing the amount of radiation emitted at different locations in the image by a radio pharmaceutical introduced into a patient's blood stream. As a result the radiation counts provide an indication of the blood volume in each image location.

Conventional edge or contour extraction techniques are applied to one of the images to determine the perimeter of a region of the heart which contains at least one chamber of the heart in the image. Preferably the perimeter is produced from an image that is likely to depict the heart at diastole and the perimeter of the left ventricle is preferred. The perimeter defines an area in each image of the series and the radiation counts within these areas are tabulated to produce a count sum for each image. The count sum of the greatest magnitude is designated as the diastolic count sum "DIAS SUM". However, if image used to produce the perimeter does not have the greatest count sum, a second perimeter is determined for the image from which produced the greatest count sum. The radiation counts within the second perimeter of its image are tabulated to produce a value that becomes the diastolic count sum (DIAS SUM).

A group of consecutively acquired images is chosen that includes an image from which the smallest radiation count sum was tabulated. In the preferred embodiment, this group consists of the the smallest radiation count sum image, two images acquired before that image, and two images acquired after that image. For each image in this group, the perimeter of the region of the heart is determined and the sum of the radiation counts within that perimeter is tabulated. The smallest magnitude sum produced for the group of images is designated as the systolic count sum "SYST SUM."

The cardiac ejection fraction then is derived from the diastolic count and systolic count sums. However before doing so, these values must be adjusted for the radiation produced by anatomical structures in front of and behind the heart, commonly referred to as "background radiation." Initially, an value is determined which corresponds to the average amount of the background radiation affecting each data sample. This average value then is multiplied by the number of picture elements within each of the diastolic and systolic perimeters to produce values designated DIAS BKGD and SYST BKGD. These latter values represent the magnitude of the background radiation affecting the diastolic count sum and systolic count sum, respectively. One technique for deriving the cardiac ejection fraction from these numerical values involves solving the expression:

$$EF = \frac{(DIAS\ SUM - DIAS\ BKGD) - (SYST\ SUM - SYST\ BKGD)}{(DIAS\ SUM - DIAS\ BKGD)}.$$

A general object of the present invention is to provide a relatively fast method for approximating the cardiac ejection fraction without having to individually determine the radiation count sums for every image taken during a cardiac cycle.

Another object is to derive the cardiac ejection fraction by finding the left ventricle perimeter in only certain images and using those perimeters to select radiation counts to sum.

DESCRIPTION OF THE PRESENT INVENTION

Figure 1:
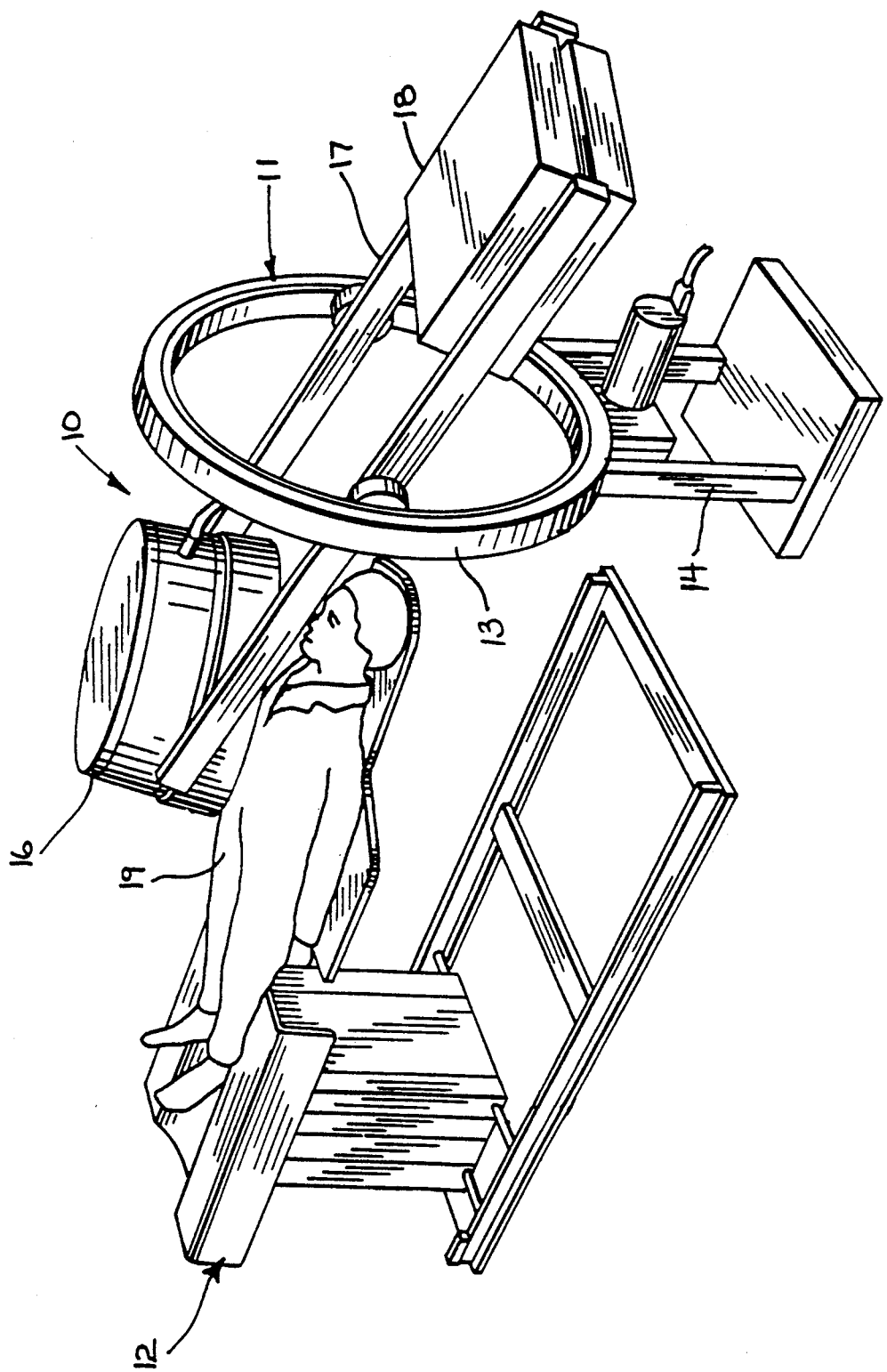
FIG. 1 is a pictorial view of a nuclear imaging scanner which employs the present invention.

With initial reference to FIG. 1, a nuclear imaging system, generally designated as 10, includes a scanner 11 and a patient support table 12. The construction and operation of the scanner 11 is similar to that shown and described in U.S. Pat. No. 4,216,381, issued on Aug. 5, 1980 and assigned to the assignee of the present invention. Briefly, the scanner 11 comprises an annular gantry 13 supported in a vertical position, as shown, by a pedestal 14 and having a camera head 16 supported from the gantry in cantilevered fashion by an arm assembly 17 and balanced by a counterweight 18. The arm assembly 17 is so connected to the gantry 13 as to allow the entire arm assembly 17 to be rotated within the gantry by a motor-drive system (not shown), to thereby rotate the camera head 16 in a circular path around the patient 19 supported on the table 12. During this operation data is gathered which can be used to reconstruct a tomographic image of the anatomical region of interest in the patient. The structure and operational movement of the scanner 11 is of a conventional nature. However, in the performance of the present invention a single image of the patient's heart is taken from a predefined fixed orientation of the camera head 16.

Image Processing Circuit

Figure 2:
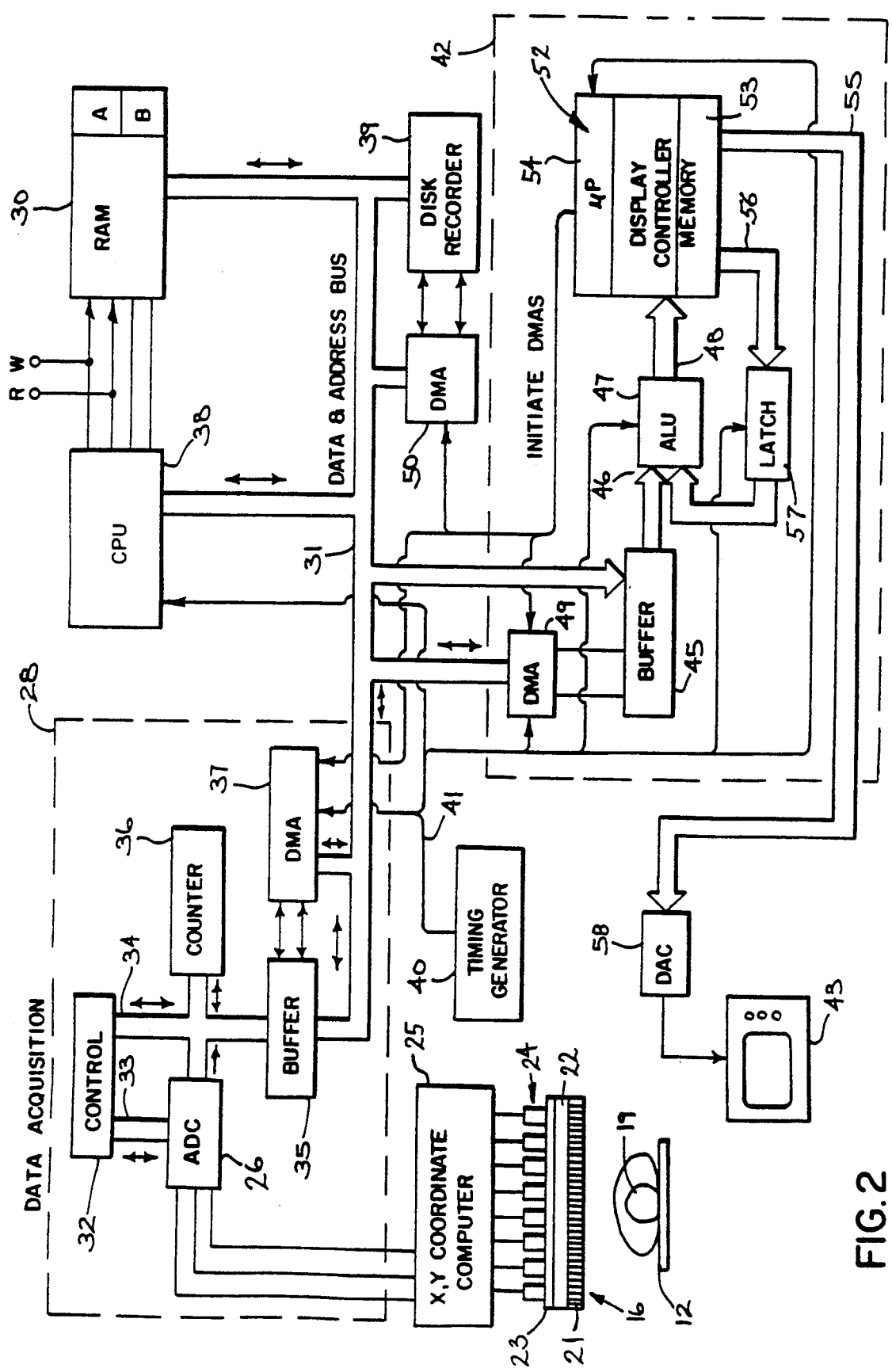
FIG. 2 is a block diagram of the image processing system for the scanner of FIG. 1.

Referring to FIG. 2, various isotopes commonly used in nuclear medicine emit gamma ray photons in a pattern which permits visualizing the configuration of body tissue and blood vessels. The nuclear or gamma camera head 16 detects and identifies the coordinates of the gamma ray photon emissions within the imaging region. The camera head comprises a lead plate 21 having a myriad of fine holes so that the plate acts as a collimator. Interfaced with the collimator is a scintillation crystal 22 which produces scintillations wherever photons are absorbed by it. The scintillations are coupled by means of a glass plate 23 to an array of photomultiplier tubes which are collectively designated by the numeral 24. The photomultiplier tubes are usually packed closely with each other in a circular or a two-dimensional array, as is well known. Any detected scintillation causes the photomultiplier tubes 24 to produce respective analog signals which are sent to a computer that is symbolized by the block marked 25.

The computer 25 uses the signals to compute the x and y coordinates of each scintillation event in terms of analog signal magnitudes. Computing the x and y coordinates in terms of analog signals also is well known with one such technique being described in U.S. Pat. No. 4,142,102. The analog x and y coordinate signals are transmitted from the computer 25 over two lines to an analog-to-digital converter (ADC) 26. A third line running from the computer 25 carries a signal, commonly called a z signal, which is indicative of whether the magnitude of the scintillation pulse was high enough or of the correct isotope to be considered a valid pulse.

ADC 26 is part of a data acquisition module which is within the boundaries of the dashed line 28. The output of ADC 26 onto a bus 34 is a series of digital number pairs which correspond to the x and y coordinates, or the addresses, of the scintillations. Each scintillation falls within the boundaries of one of the picture elements (pixels) which compose an image frame. The digital coordinate values are used as addresses to locations in a random access memory (RAM) 30 that stores the image data during acquisition.

In the frame acquisition phase, every time a pixel location in the RAM 30 is addressed, in response to a scintillation event occurring at the corresponding image position, the digital value representing the number of scintillation events at that pixel address is taken out of that location and incremented by one. The incremented value then is returned to the addressed location in RAM 30. Thus at the end of an exposure interval, the number in each memory location represents the amount of radiation emitted from the corresponding position in the patient. When an image is produced by injecting a radio pharmaceutical into the patient's blood stream, these numbers, commonly called radiation counts, represent the amount of blood in different anatomical structures of the patient.

The involvement of the data acquisition module 28 in this memory location incrementation is under the supervision of a control circuit 32. The control circuit is coupled to ADC 26 by control lines 33 and by a parallel bus 34 to a buffer 35. Buffer 35 performs the conventional functions of interchanging data between components with proper timing thereby assuring that the data is stabilized before a transfer is made. The buffer couples the bus 34 to a set of data and address buses, represented collectively by a primary bus 31 on which the legend, "data and address bus" has been applied. As will be described the primary bus 31 carries data and address signals among the components of the image processing circuitry. The data acquisition module 28 also includes an event counter 36 which tabulates the total number of scintillation events that occur during a particular exposure of the patient study. A first direct memory access (DMA) circuit 37 enables acquisition module 28 to access the storage locations in RAM 30. Every time a location in RAM 30 is to be incremented, a system central processing unit (CPU) 38 provides signals which enable the first DMA circuit 37 to make these data transfers at the proper times using the addresses from the output of ADC 26.

The RAM 30 is divided into two sectors designated A and B in FIG. 2. The gamma radiation count data are stored in one of these sectors during the acquisition interval of a given image frame as determined by the CPU 38. At the end of this frame acquisition interval, the digital numbers contained in RAM 30 have values corresponding to the amount of gamma radiation emanating from points throughout the anatomical region of interest. The acquired data for the image frame then is transferred from RAM 30 to a disk recorded 39 for storage, and to a display controller delineated by the dashed lines 42 for display on a monitor 43. The data for the next frame acquisition interval is stored in the other RAM sector. The data storage alternates between sectors A and B in RAM 30 until the system CPU 38 brings about termination of the study. This alternating storage technique enables a series of images to be acquired without interruption, while making the pixel intensity data for previous frames available from disk recorder 39 at any time. Alternatively, a relatively fast, large size RAM may be used in which the entire sequence of images is stored. In this variation, the disk recorder is used for archival purposes only and all processing is done from the images stored in the RAM 30.

A second DMA circuit 50 is associated disk recorder 39 and controls the transfer of data in and out of that device. Specifically this latter DMA circuit 50 supervises the transfer of data from RAM 30 to the disk recorder 39 as mentioned above, as well as reading image frames from disk recorder 39 for further processing. For example, the second DMA circuit 50 controls the access to the stored image frame data during the cardiac ejection fraction computation described subsequently herein. The proper timing and synchronization of these data transfers and other processing events is provided by a timing generator 40. Line 41 leading from the timing generator 40 is shown to indicate the routing of the timing signals.

The display controller 42 receives the pixel, or gamma radiation count, data for an image frame and formats the data for display as a video image on a monitor 43. When the data for a frame has been acquired, it is transferred over primary bus 31 through a buffer 45 and via bus 46 to an arithmetic logic unit (ALU) 47. A third DMA circuit 49 controls the timing of the pixel data transfer from RAM 30 to ALU 47. The output of ALU 47 is coupled by data lines 48 to an input of a display controller 52, which includes a microprocessor 54 for controlling the image display process and a memory 53 in which the processed display image data are stored. An output 56 from the display controller 52 is coupled by a data latch 57 to another input of the ALU 47. The ALU 47, besides having the capability of arithmetically manipulating the digital pixel data as it enters the display controller, can also pass the data received on bus 46 directly to the display controller memory 53 without operating on it.

Assume now that the pixel data for an image frame is stored in the memory 53 of the display controller 42. The typical display controller memory has sufficient storage locations for several 64 by 64 or one 128 by 128 pixel images. The brightness or intensity of each pixel, corresponding to the radiation counts for that image area, is represented by a multiple bit digital number in the respective display controller memory locations. The digital values must be converted into an analog video signal for display on CRT 43. The digital numbers are transferred in a raster scan sequence over bus 55 to a digital-to-analog converter (DAC) 58 where the digital data is converted into a continuous analog video signal that is applied to monitor 43 to effectuate display of the image.

Cardiac Ejection Fraction Computation

The present imaging system 10 can bve used to evaluate heart function. During the cardiac cycle the left ventricle fills with blood to a maximum volume at the diastole and then contracts to a minimum volume at the systole, thereby ejecting the blood into the arteries. The solid line in FIG. 4 graphically depicts the actual left ventricular blood volume during the cardiac cycle. Near the beginning of the curve, a maximum value occurs indicative of the blood volume at the heart diastole. Subsequently at about image frame 11 in the series, the curve reaches a minimum indicative of the heart systole, when the left ventricle has the smallest blood volume during the cardiac cycle. The cardiac ejection fraction is the average fractional decrease in blood volume between the diastole and the systole.

In order to produce a series of heart images during the cardiac cycle, a radiologist injects a radio pharmaceutical into the patient's blood stream, which emits gamma rays as it is carried throughout the patient's body by the blood flow. The patient is placed on the table 12 and camera head 16 is positioned to provide a clear view of the left ventricle in the patient's heart. As in previous systems, the image acquisition is triggered by an electrocardiogram signal so that it commences near the occurrence of a diastole. The radiation counts are accumulated in RAM 30 for a given interval and then stored in the disk recorder 39 as an image frame. At the completion of a cardiac cycle, disk recorder 39 has stored the gamma radiation count data for a plurality of image frames. Each frame includes sufficient data to produce a two-dimensional image on the display 43 which represents the intensity of the scintillation events as seen from the viewing plane of the camera head 16.

As mentioned previously, the most accurate manner to compute the cardiac ejection fraction from nuclear image data is to find the perimeter of the left ventricle in each image frame and calculate the sum of the image element radiation counts that fall within that perimeter.

If this is done for each image frame taken during the cardiac cycle, a series of count sums is produced corresponding to the left ventricle blood volume variation throughout the cardiac cycle. Once the effects of background radiation have been taken into account, the largest and smallest count sums respectively represent the diastolic and the systolic blood volumes. The cardiac ejection fraction can be calculated by determining the fractional difference between these two adjusted sums.

However, this method requires the derivation of the left ventricle perimeter and enclosed count summation for each image in the cardiac cycle, which is a relatively time consuming process even for a relatively high speed CPU 38. As a consequence, the present invention provides an approximation technique which decreases the computation time for the cardiac ejection fraction while providing a reasonably accurate result.

Figure 3:
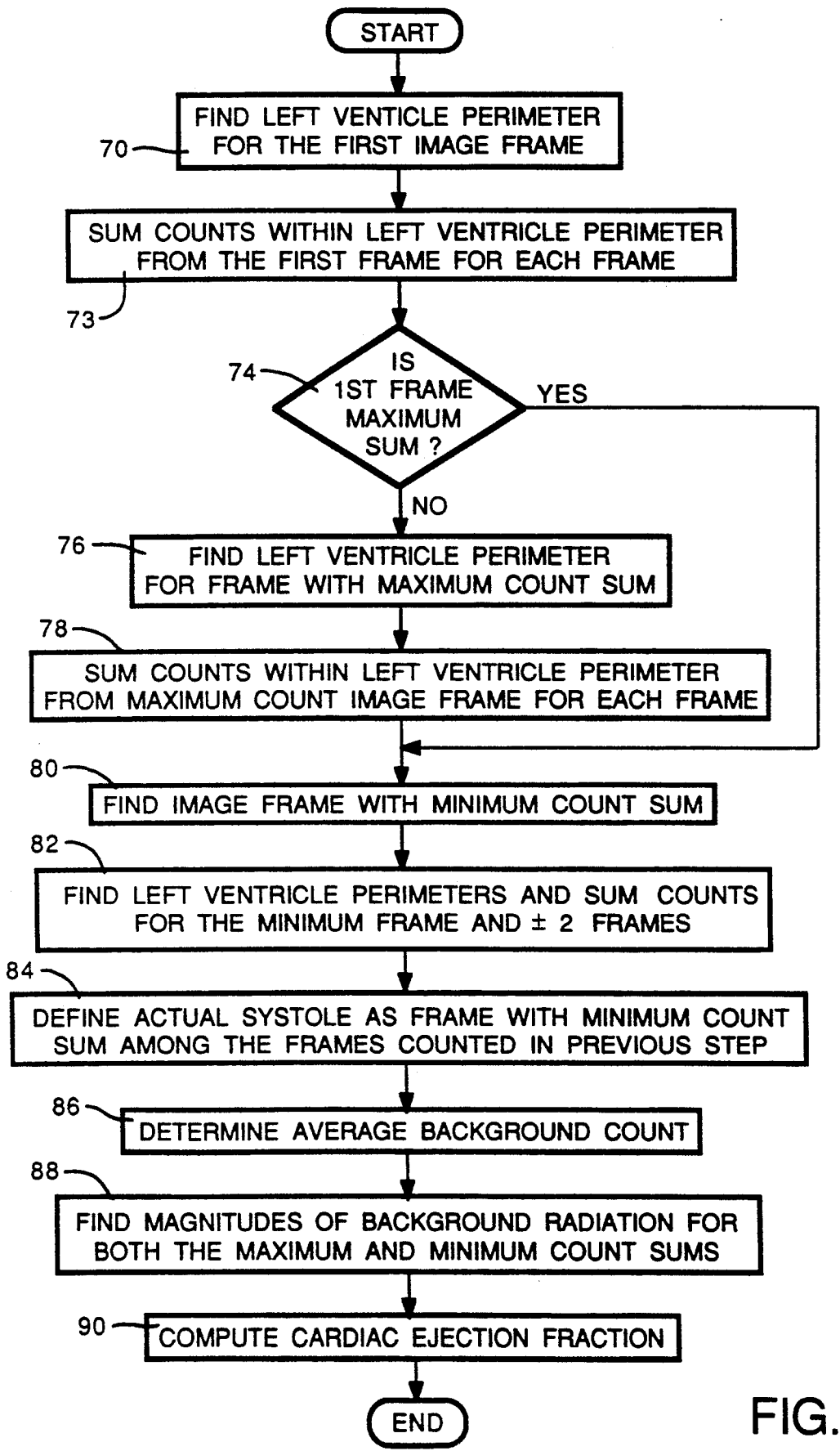
FIG. 3 is a flowchart of the process by which the cardiac ejection fraction is derived from the blood volume data.

With reference to the flowchart of FIG. 3, the present process for computing the cardiac ejection fraction commences with the CPU 38 analyzing the data for the first image frame of the sequence to find the perimeter of the left ventricle. When the CPU is analyzing an image frame, the pixel data for the frame is transferred from the disk recorder 39 to a set of storage locations in RAM 30. At step 70, the CPU 38 executes any of several well known edge finding or contour extraction routines to locate the left ventricle perimeter within the image data stored in the RAM 30. The result of step 70 provides an indication of which image element radiation counts in the first frame lie within the area of the image corresponding to the left ventricle and thereby which counts represent blood volume information from which the cardiac ejection fraction can be derived. Thereafter, the CPU 38 accesses each of the image element radiation counts lying within the left ventricle perimeter and calculates the arithmetic sum of those counts, at step 72. In doing so, the CPU 38 sequentially addresses each storage location in RAM 30 at which the left ventricle image element counts are stored. As each count is read by the CPU, it is summed with the previously read counts for that frame's left ventricle. After all of the radiation counts within the perimeter have been read, the resultant sum is stored as the initial element of a first array in a section of RAM 30. The first array is one-dimensional having an element for each of the image frames in the sequence.

The left ventricle perimeter determined for the first image frame then is employed to define areas in each of the subsequent image frames of the heart cycle. The image element radiation counts within each of these areas then are summed. Each image frame sum is stored in RAM 30 as an element of the first array. When the CPU 38 has completed executing step 72, the first array created in RAM 30 contains the radiation count sums for each image frame acquired during the heart cycle.

Figure 4:
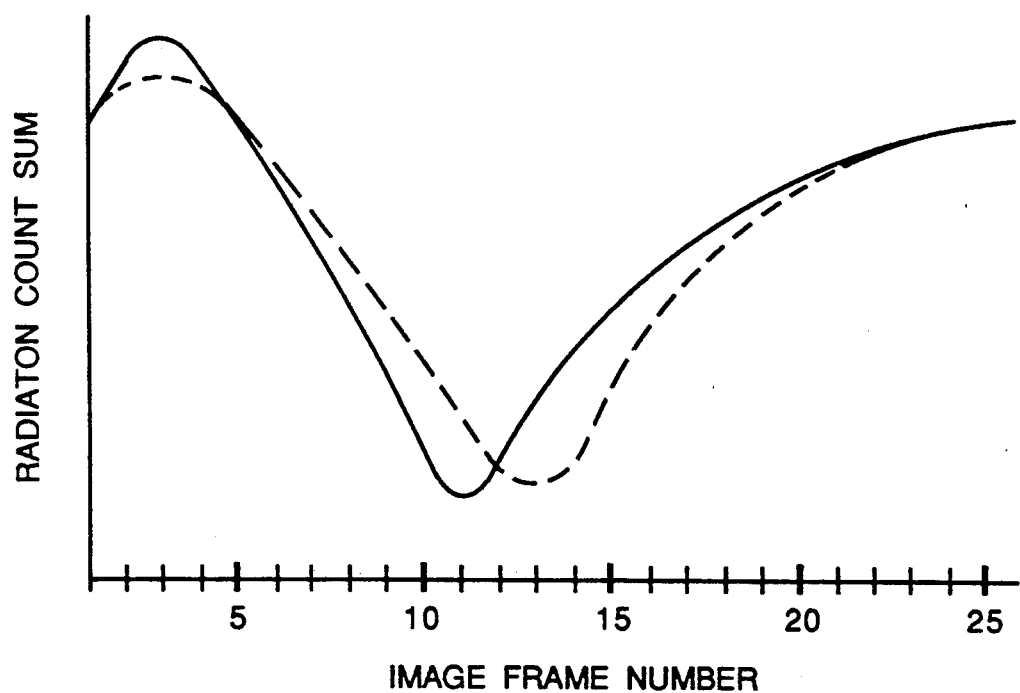
FIG. 4 graphically depicts data derived from a series of images representing the blood volume of the left ventricle during a cardiac cycle.

The count sums stored in the first array are plotted by the dashed line in FIG. 4. Note that the minimum count, indicating the systole, is produced for the thirteenth image frame by this approximation technique, whereas the actual systole occurred during the eleventh image frame as indicated by the minimum point of the solid curve. The difference represents the inaccuracy that results when the left ventricle perimeter from one image frame is to calculate the gamma radiation count sums rather that using a perimeter derived for each image frame. When the left ventricle perimeter from the first frame is applied to images which occur near the systole, other structures may enter this perimeter as the heart contracts. Therefore, the radiation count summation using this perimeter may include radiation counts resulting from blood in these other structures, such as other chambers of the heart which have entered this perimeter area of the image. The steps 74–84 of the process are directed at reducing this inaccuracy.

The program execution then advances to step 74 where the sums in the first array are compared to one another to determine whether the first frame has the largest, or maximum, count sum. Although the image acquisition commenced in response to a reference point in the electrocardiogram signal, for example the QRS complex or the R-wave, to begin image acquisition near when the diastole occurs, the first image frame may not have been taken at the actual diastole, especially in patients with heart abnormalities. For example, as shown in FIG. 4, the actual diastole occurs during the third frame interval of the sequence. In other situations, the acquisition of image frames may commence after the diastole, in which case the maximum sum will be produced from one of the latter image frames (frame 24 for example).

When the first frame of the image sequence does not contain the maximum gamma radiation count sum, the program execution branches to step 76 where the CPU 38 determines the left ventricle perimeter for the image frame having the maximum sum (e.g. the third frame in FIG. 3). The newly derived perimeter then is used to produce new values for the first array at step 78, wherein the new values are the sums of the image element counts falling within the new left ventricle perimeter in each frame of the image sequence. If the first frame was found to have the maximum count sum, the program execution bypasses steps 76 and 78. At the completion of the program sequence containing steps 72–74, a maximum count sum value designated "DIAS SUM" has been produced by the count summation from an image depicting the left ventricle at the diastole.

Next the first array of count sums is scanned by the CPU 38 at step 80 to identify the image frame containing the minimum count sum, the thirteenth frame in the example of FIG. 4. This identification is used to select a group of image frames consisting of the minimum count sum frame, a number of frames which occur in the image acquisition sequence immediately before and after the minimum count frame. Typically five or less image frames taken temporally on either side on the minimum count sum frame are selected. However, an even larger number of image frames can be chosen for this group with a corresponding increase in processing time occurring as the group increases in size. In the preferred embodiment, the selected group comprises five consecutive image frames consisting of the one for minimum count sum, the pairs of image frames which occur in the image acquisition sequence before and after the minimum count sum frame. Thus for the exemplary image sequence depicted in Figure 4, this group consists of the eleventh through fifteenth image frames. Although the group is defined by an equal number of image frames before and after the minimum count sum frame selected in step 80, an asymmetrical grouping may be used.

For each image frame in this group, the left ventricle perimeter is determined individually and the sum of image element radiation counts within that perimeter is produced at step 82. The resultant five sums are stored in a second array within RAM 30. The CPU 38 then compares the values in the second array to find the image frame having the minimum count sum within that group of five image frames. This frame is defined as depicting the actual systole and its radiation count sum is designated as the "SYST SUM," at step 84. In the example illustrated in FIG. 4, the radiation count sum for the eleventh frame becomes designated as the systolic count sum (SYST SUM).

Then at step 86, the CPU 38 determines the magnitude by which each radiation count sample is affected by gamma radiation from "background" anatomical structures that lie in front of or behind the left ventricle in each image. The techniques used to determine this background radiation count value is similar to that used in previous nuclear imaging systems and is well known to one of ordinary skill in the art. One approach defines a small region close to, but outside of, the left ventricle in the image and averages the radiation counts in this region. This produces an average amount by which each radiation count is affected by the background radiation. At step 88, this average amount is multiplied by the number of image elements that were summed to derive the diastolic count sum, DIAS SUM, which arithmetic process produces a value designated DIAS BKGD representing the affect of background radiation on the diastolic count sum. A similar process is performed to produce a value designated SYST BKGD, representing the effect of background radiation on the systolic count sum, SYS SUM.

The processing thus far has produced numerical values for the sum (DIAS SUM) of radiation counts from the left ventricle of the diastolic image frame, the sum (SYST SUM) of radiation counts of the left ventricle from the systolic image frame, and the effects of background gamma radiation on those sums (DIAS BKGD and SYST BKGD). From these values, the CPU 38 computes the cardiac ejection fraction (EF) at step 90 according to the expression:

$$EF = \frac{(DIAS\ SUM - DIAS\ BKGD) - (SYST\ SUM - SYST\ BKGD)}{(DIAS\ SUM - DIAS\ BKGD)}$$

The cardiac ejection fraction can be converted into alphanumeric characters and displayed on the monitor 43 along with other data acquired from the images or it can be sent to a computer printer.

I claim:

1. A method for deriving the cardiac ejection fraction of a patient comprising the steps of:
   (a) during a cardiac cycle, sequentially acquiring a series of electronic images, M in number, containing heart blood volume information;
   (b) defining an area which encloses heart blood volume information in one of the images;
   (c) extracting the blood volume information from the defined area in each of the images in the series and producing a first digital signal representation of blood volume for each image;
   (d) using the first digital signal representations of blood volume to determine a diastolic blood volume digital signal value;
   (e) for a plurality, P in number, of consecutive images including the image from which a smallest magnitude digital signal representation was produced, individually for each image defining an area which encloses heart blood volume information and producing a second digital signal representation of heart blood volume for that image, where P is less than M−1;
   (f) defining the second digital signal representation of blood volume which has the smallest magnitude as a systolic blood volume digital signal value; and
   (g) calculating the cardiac ejection fraction from the diastolic and systolic blood volume digital signal values.

2. The method as recited in claim 1 wherein step (d) comprises:
   if the first digital signal representation of blood volume having the greatest magnitude was produced from the image used in step (b) to define an area, then defining the first digital signal representation of blood volume produced from that image as corresponding to the diastolic blood volume digital signal value;
   otherwise performing the steps of:
   (h) defining a new area which encloses heart blood volume information in an image, designated image Q, which produced the first digital signal representation of blood volume having the greatest magnitude,
   (i) extracting the blood volume information from the newly defined area in image Q and producing a new digital signal representation of the blood volume for image Q, and
   (j) defining the new digital signal representation of the blood volume as corresponding to the diastolic blood volume digital signal value.

3. The method as recited in claim 1 wherein the number M is at least sixteen, and the number P is less than eight.

4. The method as recited in claim 1 wherein the number M is greater than sixteen, and the number P is five.

5. The method as recited in claim 1 wherein the cardiac ejection fraction is calculated according to the expression:

$$EF = \frac{DIASTOLIC\ VALUE - SYSTOLIC\ VALUE}{DIASTOLIC\ VALUE}$$

where DIASTOLIC VALUE is the diastolic blood volume digital signal value, and SYSTOLIC VALUE is the systolic blood volume digital signal value.

6. A method for deriving the cardiac ejection fraction of a patient comprising the steps of:
   (a) during a cardiac cycle, acquiring a sequence of images, numbered by integers 1 through M, in which each image contains heart blood volume information;
   (b) storing the acquired images in a memory means;
   (c) defining an area in one of the stored images, designated image N, which area substantially encloses heart blood volume information;
   (d) extracting the blood volume information from the defined area in each of the M stored images to produce a digital signal representation of blood volume for each image;
   (e) defining a digital signal representation of blood volume as representing diastolic blood volume;
   (f) identifying an image, designated by integer R, from which was produced a digital signal representation of blood volume having the smallest magnitude;
   (g) for each image of a sequence of consecutive images numbered R−S through R+T, where S and T are non-negative integers, individually defining an area in each image which encloses heart blood volume information and producing another digital signal representation of heart blood volume;

(h) defining a digital signal representation of heart blood volume within the ones produced in step (g), which has the smallest magnitude, as representing systolic blood volume; and (i) calculating the cardiac ejection fraction from the diastolic and systolic blood volume digital signal values.

7. The method as recited in claim 6 wherein step (e) comprises:

if the digital signal representation of blood volume which has the greatest magnitude was produced from image N, then defining the digital signal representation of blood volume from image N as representing diastolic blood volume;

otherwise performing the following steps:

defining an new area which substantially encloses the heart blood volume information in an image, designated by integer Q, which produced the digital signal value corresponding to the blood volume having the greatest magnitude;

extracting the blood volume information from the newly defined area in image Q, and producing a new digital signal representation of the blood volume depicted in image Q; and defining the new digital signal representation of the blood volume as representing diastolic blood volume.

8. The method as recited in claim 6 wherein S and T each has a integer values between one and five.

9. A method for deriving the cardiac ejection fraction of a patient comprising the steps of:

(a) sequentially acquiring series of nuclear images of a heart during a cardiac cycle in which each image is formed by a plurality of radiation counts;

(b) as each image of the series is acquired, storing the image in a memory;

(c) defining a perimeter of the left ventricle of the heart in one of the images stored in the memory;

(d) for each image of the series, summing the radiation counts located in the image within the previously defined perimeter;

(e) if the image for which the perimeter was defined in step (c) does not have the largest sum of the radiation counts, then defining a new perimeter of the left ventricle of the heart in the stored image which has the largest sum as calculated at step (d) and producing a new sum of the radiation counts located within the new perimeter in this latter image, this new sum being designated "DIAS SUM", otherwise the sum having the greatest magnitude calculated at step (d) being designated "DIAS SUM";

(f) individually for each image, in a group of consecutive images that includes the image from which a smallest radiation count sum is calculated at step (d), defining a perimeter of the left ventricle of the heart and summing the radiation counts within that perimeter, the radiation count sum produced in the present step which has the smallest magnitude being designated "SYST SUM"; and (g) calculating the cardiac ejection fraction in response to the DIAS SUM and the SYST SUM.

10. The method as recited in claim 9 further comprising:

determining an amount (DIAS BKGD) by which background radiation affects the value of DIAS SUM;

determining an amount (SYST BKGD) by which background radiation affects the the value of SYST SUM; and wherein the step of calculating the cardiac ejection fraction also is in response to the DIAS BKGD and the SYST BKGD.

11. The method as recited in claim 10 wherein the cardiac ejection fraction is calculated according to the expression:

$$EF = \frac{(DIAS\ SUM - DIAS\ BKGD) - (SYST\ SUM - SYST\ BKGD)}{(DIAS\ SUM - DIAS\ BKGD)}.$$

12. The method as recited in claim 9 where in step (f) the group of consecutive images further includes two images that were acquired just prior to the image from which a smallest radiation count sum is calculated, and two images that were acquired just after the image from which a smallest radiation count sum is calculated.

13. The method as recited in claim 1 wherein the step of extracting blood volume information comprises summing radiation counts located in the image within the previously defined area.

14. The method as recited in claim 6 wherein the heart blood volume information is represented by radiation counts in the image; and step of extracting blood volume information comprises summing the radiation counts located in the image within the previously defined area.

* * * * *